United States Patent [19]
Chou et al.

[11] Patent Number: 5,886,185
[45] Date of Patent: Mar. 23, 1999

[54] POLYAMINE-LINKED ACRIDINE DIMERS

[75] Inventors: Shan-Yen Chou, Taipei; Shan-Shue Wang, Tainan; Chin-Fen Lee, Keelung; Wei-Kun Yin, Taichung; Shyh-Fong Chen, Taipei, all of Taiwan

[73] Assignee: Development Center for Biotechnoloy, Taiwan

[21] Appl. No.: 974,473

[22] Filed: Nov. 20, 1997

[51] Int. Cl.$^6$ .................................................. C07D 219/12
[52] U.S. Cl. .............................................................. 546/106
[58] Field of Search ............................................... 546/106

[56] References Cited

PUBLICATIONS

Barbet et al., Pharmacologie Molécularie–Composés de Poly–intercalation de l'ADN, *C.R. Acad. Sc. Paris,* Série D, pp. 851–853, 1975 (with English abstract).

Le Bret et al., A reexaminationof the problem of resonance enery transfer between DNA intercalated chromophores using bisintercalating compounds, *Nucleic Acids Research,* 4:5, pp. 1361–1376, 1977.

Jacquemin–Sablon et al., Yeast Mitochondrial Deoxyribonuclease Stimulated by Ethidium Bromide. 2. Mechanism of Enzyme Activation, *Biochemistry,* 18:1, pp. 128–134, 1979.

Kraayenhof et al., On the interaction of 9–amino–substituted acridine probes with energy–conserving membranes, *Dynamics of Energy–Transducin Membranes,* Elsevier Scientific Publishing Co., New York, 1974.

LePecq et al., DNA polyintercalating drugs: DNA binding of diacridine derivatives, *Proc. Nat. Acad. Sci,* 72:8, pp. 2915–1919, 1975.

Markovits et al., Acridine dimers: influence of the intercalatin ring and of the linkin–chain nature on the equilibrium and kinetic DNA–binding parameters, *Eur. J. Biochem,* 180, pp. 359–366, 1989.

Denny WA et al. J. Med. Chem. 28 (11), 1568–74, 1985.

Hansen JB et al. J. Med. Chem. 26 (10), 1510–14, 1983.

Ackerman NB et al. J. Med. Chem. 11 (2), 315–21, 1968.

Wirth M et a. J. Am. Chem. Soc. 110 (3), 932–39, 1988.

Elslager EF. et al. Synthetic Amebicides VIII 5(5), 599–607, 1968.

*Primary Examiner*—Evelyn Huang
*Attorney, Agent, or Firm*—Fish & Richardson

[57] ABSTRACT

A series of novel polyamine-linked acridine dimers and derivatives thereof are described. The polyamine-linked acridine dimers and derivatives are potential anti-cancer agents.

16 Claims, No Drawings

POLYAMINE-LINKED ACRIDINE DIMERS

BACKGROUND OF THE INVENTION

The invention relates to novel derivatives of polyamine-linked acridines and salts thereof and the processes and intermediates for their preparation.

DNA intercalating drugs are a class of antitumor agents that interact with the DNA double helix. DNA intercalating drugs include synthetic intercalating drugs, anthracyclines and other intercalating antitumor antibiotics.

Several antitumor agents are traditionally clinically useful, such as actinomycin D, adriamycin and daunomycin. Recently, several intercalating antitumor agents were also developed or under clinical trials. Amsacrine, an aminoacridine, and mitoxantrone hydrochloride, an anthracenedione, are synthetic intercalating drugs that were launched in 1982 and 1984, respectively. Bisanthrene hydrochloride, an anthracene bishydrazone cytostatic intercalant, was launched in 1989 for the treatment of nonlymphocytic leukemia. Three examples of anthrapyrazoles under clinical trial include: piroxantrone; iosoxantrone hydrochloride; and teloxantrone. Other synthetic DNA intercalating antitumor drugs include crisnatol mesylate, polyamine-linked naphthalimide antitumor agents, quinobenzoxazine antineoplastic compounds, and aza-anthracenedione antitumor agents.

DNA polyintercalating drugs based on polyamine-linked acridine dimers have been shown to be fluorescent probes of DNA sequence. See, Le Pecq, J. B., Le Bret, M., Barbet, J., Roques, B. *Proc.Nat.Acad.Sci*, USA Vol.72. No.8. 2915 (1975). The effect of the rigidity of the polyamine linking chain on the DNA-intercalating properties were also studied. See, Markovits, J., Garbay-Jaureguiberry, C., Roques, B., Le Pecq, J. B. *Eur. J. Biochem.* 180, 359 (1989). One can consider these drugs to consist of a DNA intercalation domain (i.e., the acridine ring region) and a protein binding domain (i.e., sidearms or linkers).

SUMMARY OF THE INVENTION

The present invention features compounds of formula I

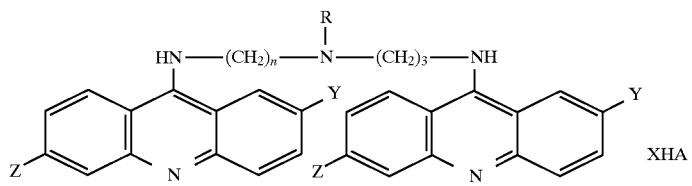

wherein:
n is 3, 4, 5, or 6; X is between 0 and 5, inclusive; Z is H, F, Cl, Br, or I; Y is H or OR', wherein R' is H or $C_{1-4}$ alkyl; A is $OC(O)CH_3$, $OC(O)CF_3$, $OSO_2CH_3$, or halogen; and R is hydrogen, $C_{1-10}$ alkyl, $C_{1-10}$ hydroxyalkyl, $C_{1-10}$ polyhydroxyalkyl, $C_{1-10}$ aminoalkyl, $C_{1-10}$ aminohydroxyalkyl, $C_{1-10}$ haloalkyl, or $(CH_2)_yR''$, wherein y is an integer between 1, 2 or 3, and R" is aryl, substituted aryl, heteroaryl, substituted heteroaryl, heterocyclyl, or substituted heterocyclyl; with the proviso that when R is hydrogen, X is between 1 and 5, inclusive.

The term "halogen" used herein refers to a halogen atom such as fluorine, chlorine, bromine, or iodine.

The term "$C_{1-10}$ alkyl" used herein refers to a linear, cyclic, or branched alkyl group containing 1–10 carbon atoms, including but not limited to methyl, ethyl, cyclopropyl, cyclopropylmethyl, n-propyl, i-propyl, n-butyl, t-butyl, amyl, or amylmethyl. The $C_{1-10}$ alkyl can be substituted to form a hydroxyalkyl, polyhydroxyalkyl, aminoalkyl, aminohydroxyalkyl, or haloalkyl, including, but not limited to, 2,3-di(hydroxy)propyl.

The term "$(CH_2)_yR''$" used herein refers to a $C_{1-10}$ fragment having a phenyl ring, a phenyl ring with one or more substituents, a heteroaryl ring, a heteroaryl ring both one or more substituents, a heterocyclyl ring, or a hetrocyclyl ring with one or more substituents which is linked to the dialkyl amine nitrogen atom by a "—$(CH_2)_y$—" moiety via one of the ring atoms, arbitrarily assigned to be "1" position. In each case the substituent can be hydroxy, aryl, substituted aryl, $C_1$–$C_4$ alkyl, amino, substituted amino, or $C_1$–$C_4$ alkoxy. The $(CH_2)_yR''$ group, where R" is aryl or substituted aryl, can be, but is not limited to, $CH_2C_6H_5$, $(CH_2)_2C_6H_5$, $(CH_2)_3C_6H_5$, $CH_2C_6H_4(2'-OMe)$, $CH_2C6H_3(2',3'-diOMe)$, $CH_2C_6H_2(3,4,5,-triOMe)$, $CH_2C_6H_4(4'-Cl)$, or $CH_2C_6H_3(2,4'-diF)$. The R" group wherein R" is a heteroaryl or substituted heteroaryl can be, but is not limited to, furyl, pyridyl, thienyl, pyrrolyl, a $C_{1-4}$ alkyl-substituted furyl, a $C_{1-4}$ alkyl-substituted pyrrolyl, a $C_{1-4}$ alkyl-substituted thienyl, a $C_{1-4}$ alkyl-substituted pyridyl, an aryl-substituted furyl, a substituted aryl-substituted furyl, a halogen-substituted furyl, a halogen-substituted pyridyl, a halogen-substituted thienyl (e.g., 2'-furyl, 2'-pyridyl, 2'-thienyl, 2'-pyrrolyl, 3'-furyl, 3'-pyridyl, 3'-thienyl, 3'-pyrrolyl, and derivatives thereof). The R" group where R" is a heterocyclyl ring or substituted heterocyclyl ring can be, but is not limited to carbohydrate, dioxolanyl, oxazolidinyl, substituted carbohydrate, substituted dioxolanyl, or substituted oxazolidinyl.

Two separate synthetic routes can be employed for the preparation of the polyamine-linked acridine dimers. The dimers can contain a regiospecific orientation of each substituent at the central nitrogen of the polyamine linker.

The polyamine-linked acridine dimers set forth above which can be used to treat tumors (e.g., leukemia, colon cancer, and other cancers), a method of treating a tumor by administering to a patient the just-described pharmaceutical composition is also contemplated as an aspect of this invention. Within this invention too is the use of polyamine linked acridine dimers for the manufacture of a medicament for the treatment of tumor.

Other features or advantages of the present invention will be apparent from the following detailed description and also from the appending claims.

DETAILED DESCRIPTION OF THE INVENTION

In general, the present invention provides the compounds of formula I described above. The preparation methods and the cytotoxicities of compounds of formula I are described. The in vitro cytotoxicities were evaluated against COLO 205, HA22T, $SKBR_3$ and MOLT-4 cell lines. In addition, the in vivo antitumor activity of selected compounds was examined.

In another aspect, the present invention provides two separate routes for synthesizing the compounds of formula I. One method involves contacting (e.g., condensing) an N-substituted-N,N-bis(3-aminopropyl)amine with 6,9-dichloro-2-methoxy-acridine under basic conditions to form the compound of formula I wherein X is 0, and followed by salt formation between the compound of formula I wherein X is 0, and the appropriate number of equivalents of acid HA to give a compound of formula I wherein X is between 1 and 5. The N-substituted-N,N-bis(3-aminopropyl)amine can be obtained commercially or prepared by reductive-amination of 3,3'-iminodipropionitrile with appropriate aldehyde and followed by nitrile reduction. See, e.g., Scheme 1.

A second method involves reductive-amination of the compound of formula I, wherein R is H, n is 3 or 4, and X is 0, with an appropriate aldehyde to form a compound of formula I, wherein R is not H and X is 0, and followed by salt formation between the compound of formula I, wherein X is 0, and appropriate equivalent of acid HA to give formula I, wherein X is between 1 and 5. The compounds of formula I, wherein R is H and X is 0, were prepared by condensation of N,N-bis(3-aminopropyl)amine or spermidine with 6,9-dichloro-2-methoxy-acridine under basic conditions. Preferably, the condensation of N,N-bis(3-aminopropyl)amine and 6,9-dichloro-2-methoxy-acridine takes place by heating (i.e., at 118° C.) in DMF using potassium carbonate as the base to give formula I, wherein, R is H, n is 3 and X is 0, in 60% isolated yield. It is difficult to obtain the target compound in reasonable yield by the method described in literature, e.g., using phenol as the solvent, as described in Barbet, J., Roques, B. P., Le Pecq, J. B. *C.R.Acad. Sci. Paris* 2810, 851 (1975). See, e.g., Scheme 2.

The cytotoxicities of most of the derivatives are comparable to or more potent than that of adriamycin. The compounds are highly potent against, for example, the MOLT-4 cell line ($IC_{50}$ is <0.01 μg/mL). Among these derivatives, the (cyclopropyl)methyl-, (3'-methyl-2'-thienyl)methyl- and (2'-pyridyl)methyl-derived polyamine-linked acridine dimers are very selective against, for example, the COLO 205 cell line ($IC_{50}$ is 0.01 or <0.01 μg/mL).

The water solubilities of the salts are greatly improved over the free-base forms. Thus, the compounds of formula I suitable for use in vivo.

The solubility tests of some salt derivatives are listed in Table I.

ing a tumor. As used herein, an effective amount of the polyamine-linked acridine dimers is defined as the amount of the compound which, upon administration to a patient, inhibits growth of tumor cells, kills malignant cells, reduces the volume or size of the tumors, or eliminates the tumor entirely in the treated patient. The effective amount to be administered to a patient is typically based on body surface area, patient weight, and patient condition. The interrelationship of dosages for animals and humans (based on milligrams per meter squared of body surface) is described by Freireich, E. J., et al., Cancer Chemother. Rep., 50(4):219, 1966. Body surface area may be approximately determined from patient height and weight. See, e.g., Scientific Tables, Geigy Pharmaceuticals, Ardley, N.Y., pages 537–538, 1970. An effective amount of the polyamine-linked acridine dimers in the present invention can range from about 5 mg/kg to about 500 mg/kg, more preferably from about 5 mg/kg to about 250 mg/kg, and most preferably about 5 to about 150 mg/kg. Effective doses will also vary, as recognized by those skilled in the art, dependant on route of administration, excipient usage, and the possibility of co-usage with other therapeutic treatments including other anti-tumor agents, and radiation therapy.

The pharmaceutical formulation may be administered via the parenteral route, including subcutaneously, intraperitoneally, intramuscularly and intravenously. Examples of parenteral dosage forms include aqueous solutions of the active agent, in a isotonic saline, 5% glucose or other well-known pharmaceutically acceptable liquid carrier.

Solubilizing agents such as cyclodextrins, which form specific, more soluble complexes with the present polyamine-linked acridine dimers, or other solubilizing agents well-know to those familiar with the art, can be utilized as pharmaceutical excipients for delivery of the therapeutic compounds.

The polyamine-linked acridine dimer can also be formulated into dosage forms for other routes of administration utilizing well-known methods. The pharmaceutical composition can be formulated, for example, in dosage forms for oral administration in a capsule, a gel seal or a tablet. Capsules may comprise any well-known pharmaceutically acceptable material such as gelatin or cellulose derivatives. Tablets may be formulated in accordance with the conventional procedure by compressing mixtures of the active polyamine-linked acridine dimer and a solid carrier, and a lubricant. Examples of solid carriers include starch and sugar bentonite. The polyamine-linked acridine dimer can also be administered in a form of a hard shell tablet or

TABLE I

| | Water solubility (mg/mL) |
|---|---|
| R is H, Y is Cl, Z is OMe, n is 3, X is 0 | 0 |
| R is H, Y is Cl, Z is OMe, n is 3, A is OC(O)CH$_3$, X is 5 | 8 |
| R is H, Y is Cl, Z is OMe, n is 3, A is Cl, X is 5 | 0 |
| R is CH$_3$, Y is Cl, Z is OMe, n is 3, A is O(CO)CH$_3$, X is 5 | 10 |
| R is CH$_3$, Y is Cl, Z is OMe, n is 3, A is Cl, X is 5 | 0 |

As mentioned above, the present invention provides a pharmaceutical formulation having an effective amount of a polyamine-linked acridine dimers for treating a patient havcapsule containing, for example, lactose or mannitol as a binder and a conventional filler and a tableting agent.

The carrier in the pharmaceutical composition must be "acceptable" in the sense of being compatible with the active ingredient of the formulation (and preferably, capable of stabilizing it) and not deleterious to the subject to be treated.

The antitumor activity of polyamine linked acridine dimer described above can be preliminarily evaluated using an in vitro assay, and then confirmed by in vivo testing.

Without further elaboration, it is believed that one skilled in the art can, based on the description herein, utilize the present invention to its fullest extent. The following specific examples are, therefore, to be construed as merely representative, and not limitative of the remainder of the disclosure in any way whatsoever. All publications cited in this disclosure are incorporated by reference.

Examples 1–55 represent typical syntheses as exemplified in Scheme 1 and 2. 9-Chloroacridine derivatives such as 6,9-dichloro-2-methoxyacridine can be prepared by the method described in Schulenberg, Archer in Organic Reaction vol. 14 (New York 1968), p. 19. This compound can react with a polyamine to form a polyamine-linked acridine dimer. Reductive amination can be used to make the chain derivatives. These examples are understood to be illustrative only. For example, different polyamines or other acridine derivatives can be used to make other acridine dimers.

Examples 56–58 represent in vitro cytotoxicity screening, DNA intercalating assays, and in vivo antitumor activities of polyamine-linked acridine dimers.

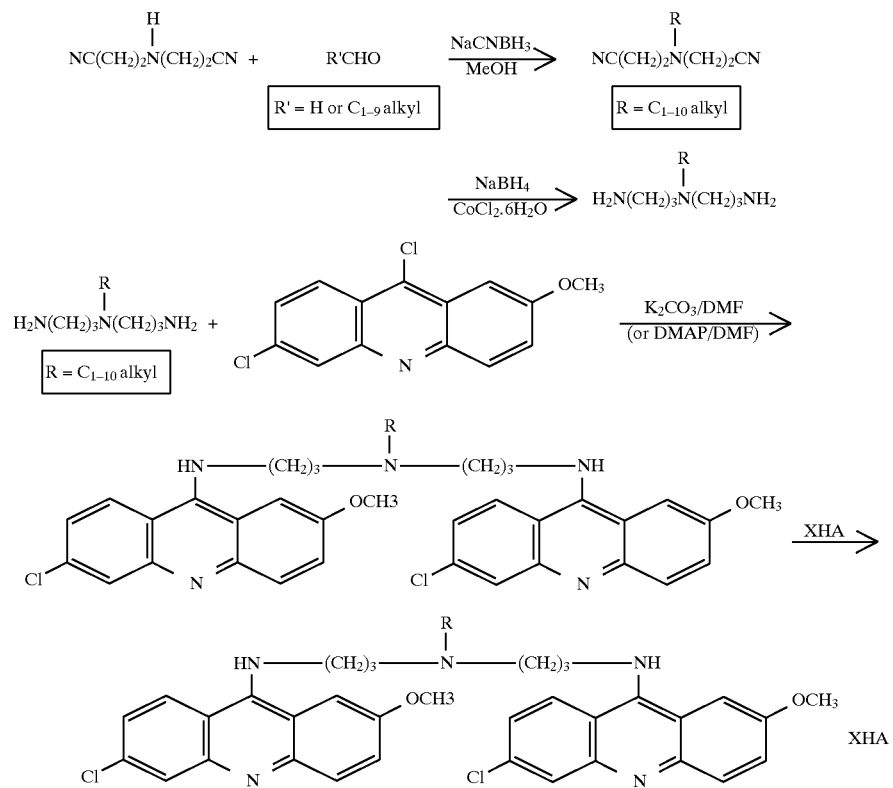

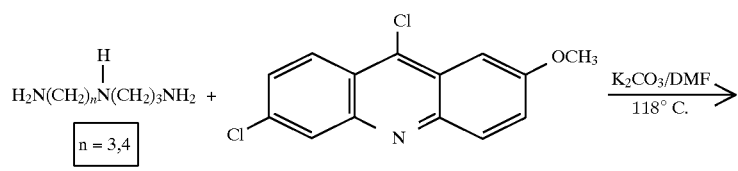

-continued
Scheme 2

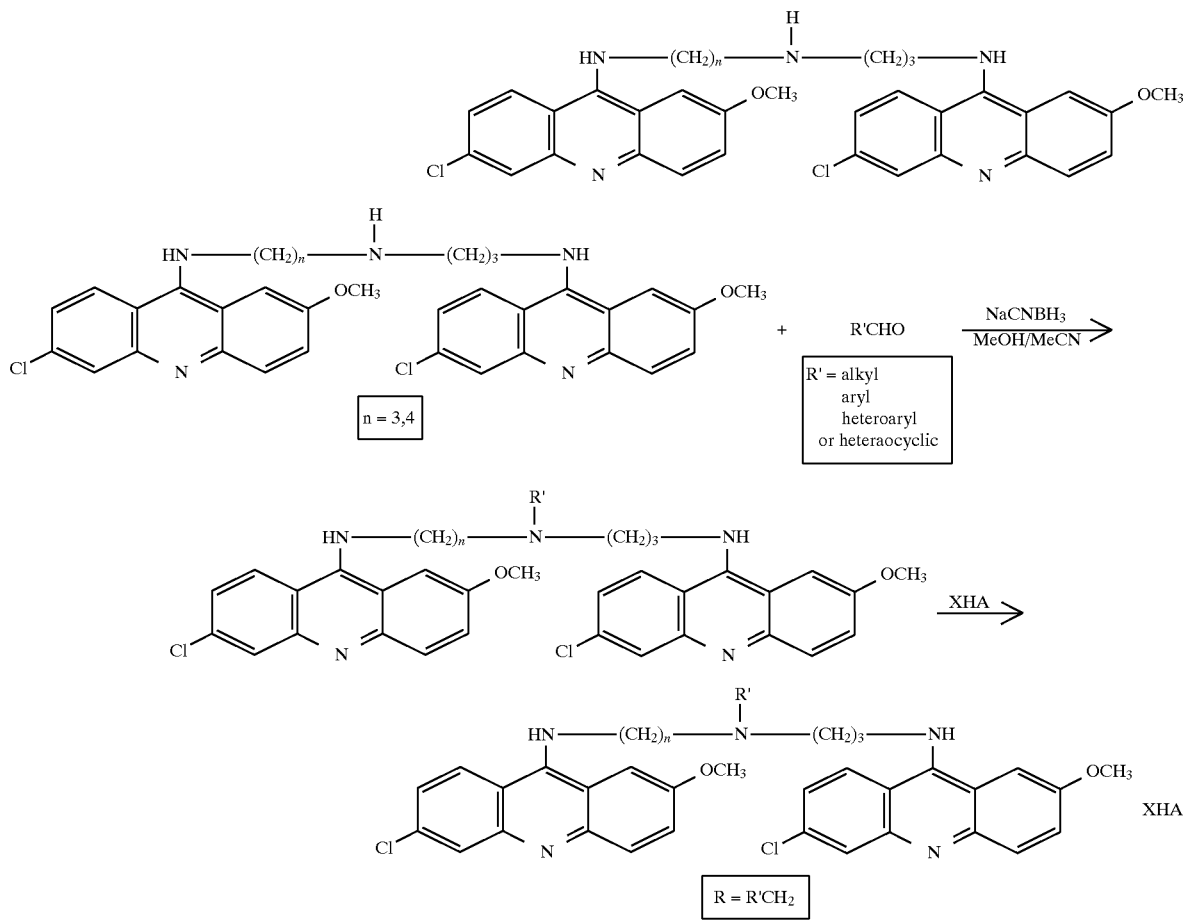

EXAMPLE 1

3-[N-(2-Cyano-ethyl)-N-ethyl-amino]-propionitrile

To a stirred mixture of 3,3'-iminodipropionitrile (14.4 g, 0.117 mol), acetaldelyde (25.7 g, 0.584 mol), methanol 50 mL), and acetonitrile (400 mL) was added sodium cyanoborohydride (9.6 g, 0.152 mol). The mixture was allowed to stir at room temperature overnight. The solvent was evaporated. The resulting residue was partitioned between dichloromethane and $H_2O$. The dichloromethane layer was washed with water, dried, and evaporated to give a yellow oil, which was distilled by a Kugelrohr apparatus to give the title compound (9.2 g, 52%). $^1$H NMR (CDCl$_3$, 200 MHz) 2.86 (t, J=7.0 Hz, 4H), 2.64 (q, J=7.0 Hz, 4H), 2.48 (t, J=7.0 Hz, 4H), 1.08 (t, J=7.0 Hz, 3H).

EXAMPLE 2

3-[N-(2-Cyano-ethyl)-N-cyclopropylmethyl-amino]-propionitrile

The title compound was prepared from 3,3'-iminodipropionitrile and cyclopropanecarboxaldehyde by the method described in Example 1 in comparable yield. $^1$H NMR (CDCl$_3$, 200 MHz) 2.86 (t, J=7.0 Hz, 4H), 2.42 (t, J=7.0 Hz, 4H), 2.39 (d, J=7.2 Hz, 1H), 0.75 (m, 1H), 0.45 (m, 2H), 0.06 (m, 2H).

EXAMPLE 3

N-[1-(3-Amino-propyl)-N-1-(ethyl)]-propane-1,3-diamine

To a solution of 3-[N-(2-Cyano-ethyl)-N-ethyl-amino]-propionitrile (15.1 g, 0.1 mol) and cobaltous chloride hexahydrate (47.6 g, 0.2 mol) in methanol (600 mL) was added sodium borohydride (38 g, 1.0 mol) in portions with stirring at 20° C. To the mixture was added 200 mL of 3N hydrochloric acid. After removal of methanol by distillation and unreacted nitrile by extraction with ether, the aqueous layer was made alkaline by addition of a concentrated ammonium hydroxide solution which was then extracted with 100 mL of ethyl acetate three times. The combined organic extracts were washed with brine, dried over sodium sulfate, and the solvent evaporated to give the title compound (9.6 g, 60%).

EXAMPLE 4

N-[1-(3-Amino-propyl)]-N-[1-(cyclopropylmethyl)]-propane-1,3-diamine

The title compound was prepared from 3-[N-(2-Cyano-ethyl)-N-cyclopropylmethyl-amino]-propionitrile by the method described in Example 3 in comparable yield. $^1$H NMR (CDCl$_3$, 200 MHz) 2.50–3.00 (m, 8H), 2.30 (d, J=6.4 Hz, 2H), 1.60 (m, 4H), 0.90 (m, 1H), 0.50 (m, 2H), 0.12 (m,

EXAMPLE 5

Formula I (wherein R=H, n=3, Z=Cl, Y=OMe, and X=0)

A mixture of 6,9-dichloro-2-methoxy-acridine (20 g, 71.91 mmol), 3,3'-diaminodipropylamine (5.5 g, 41.9 mmol) and potassium carbonate anhydrous (20 g, 144.9 mmol) in DMF (200 mL) were stirred at 118° C. for 16 hours. The resulting solution was filtered and distilled on vacuum to remove DMF. The residue was triturated with dichloromethane-$H_2O$ and filtered, the yellow powder was fiurer triturated with acetone (250 mL) to give 8.6 g of the title compound. The mother liquid crystallized upon standing at 0° C., which was filtered and triturated with acetone to give 3.0 g of the title compound. The mother liquid was evaporated and chromatographed using 1:10:0.1 (v/v) methanol-ethyl acetate-triethylamine to give the 1.6 g of the title compound. The combined yield is 13.2 g (59.74%). MP 157°–159° C. $^1$H NMR (DMSO-$d_6$, 500 MHz) 8.28 (d, J=9.25 Hz, 2H), 7.81 (S,2H), 7.77 (d, J=9.25 Hz, 2H), 7.56 (s,2H), 7.35 (d, J=9.25 Hz, 2H), 7.17 (d, J=9.25 Hz, 2H), 3.87 (s, 6H), 3.79 (t, J=6.43 Hz, 4H,) 2.69 (t, J=6.43 Hz, 4H), 1.85 (m, 4H). The compound was identical in all respects with the material prepared by the method described in Barbet, J, Roques, B. P., LePecq, J. B. *C.R.Acad. Sci. Paris* 2810, 851.

EXAMPLE 6

Formula I (wherein R=H, n=3, X=4, Z=Cl, Y=OMe, and A=OC(O)$CH_3$)

A mixture of the compound of formula I (wherein R=H, n=1, and X=0, see Example 5) (0.25 g, 0.41 mmol), acetic acid (77.32 mg, 1.30 mmol) and methanol (20 ml) was stirred at refluxing temperature until the mixture became homogeneous (about 10 minutes). The mixture was filtered, evaporated and the residue was triturated with diethyl ether afforded the title compound (0.33 g, 95%), MP 161.2°–162.8° C., $^1$H NMR (DMSO-$d_6$, 500 MHz) 8.29 (d, J=9.3 Hz, 2H), 7.82 (s, 2H), 7.78 (d, J=9.3 Hz, 2H), 7.59 (s, 2H), 7.38 (d, J=9.3 Hz, 2H), 7.25 (d, J=9.3 Hz, 2H), 3.88 (s, 6H), 3.79 (m, 4H), 2.72 (m, 4H), 1.89 (s, 12H), 1.88 (m, 4H).

EXAMPLE 7

Formula I (wherein R=H, n=3, X=5, Z=Cl, Y=OMe, and A=OC(O)$CF_3$)

Using trifluoroacetic acid (500 mol %) as the acid, the title compound was obtained in comparable yield by the method described in Example 6. MP 189.6°–191.2° C., $^1$H NMR (DMSO-$d_6$, 500 MHz) 8.47 (d, J=9.0 Hz, 2H), 7.90 (br s, 4H), 7.85 (d, J=9.0 Hz, 2H), 7.33 (d, J=9.0 Hz, 2H), 7.50 (d, J=9.0 Hz, 2H), 4.19 (br s, 4H), 3.95 (s, 6H), 3.09 (br s, 4H), 2.23 (br s, 4H).

EXAMPLE 8

Formula I (wherein R=H, n=3, X=1, Z=Cl, Y=OMe, and A=OS(O)$_2$$CH_3$)

Using methanesulfonic acid (100 mol %) as the acid, the title compound was obtained in comparable yield by the method described in Example 6. MP 85°–86° C., $^1$H NMR (DMSO-$d_6$, 500 MHz) 8.30 (d, J=9.3 Hz, 2H), 7.81 (s, 2H), 7.76 (d, J=9.3 Hz, 2H), 7.60 (s, 2H), 7.44 (d, J=9.3 Hz, 2H), 7.30 (d, J=9.3 Hz, 2H), 3.90 (s, 6H), 3.85 (m, 4H), 2.96 (m, 4H), 2.38 (s, 3H), 1.99 (m, 4H).

EXAMPLE 9

Formula I (wherein R=H, n=3, X=5, Z=Cl, Y=OMe, and A=Cl)

The title compound was prepared by treating the free base (see Example 5) with excess aqueous HCl. MP 294°–296° C.

The following compounds were prepared by the methodology described in Examples 1 through 9.

EXAMPLE 10

Formula I (wherein R=H, n=4, Z=Cl, Y=OMe, and X=0)

The title compound was prepared from spermidine by the methodology described in Example 5 in comparable yield. MP 163°–165° C., $^1$H NMR (CDCl$_3$, 500 MHz) 7.70–8.00 (m, 6H), 7.10–7.40 (m, 6H), 3.85–3.88 (m, 8H), 3.71 (m, 2H), 2.86 (m, 2H), 2.70 (m, 2H), 1.88 (m, 2H), 1.81 (m, 2H), 1.68 (m, 2H).

EXAMPLE 11

Formula I (wherein R=H, n=4, X=5, Z=Cl, Y=OMe, and A=Cl)

MP 290°–291° C., $^1$H NMR (DMSO-$d_6$, 500 MHz) 8.54 (m, 2H), 8.07(m, 2H), 7.94 (d, J=9.2 Hz, 2H), 7.87 (d, J=9.2 Hz, 2H), 7.65 (d, J=9.2 Hz, 2H), 7.48 (m, 2H), 4.22 (br s, 2H), 4.10 (br s, 2H), 3.96 (s, 6H), 3.06 (br s, 2H), 2.97 (br s,2H), 2.30 (m, 2H), 1.99 (m, 2H), 1.77 (m, 2H).

EXAMPLE 12

N-alkylated polyamine-linked acridine dimers were prepared according to the method shown in Scheme 1.
Typical example:

Formula I (wherein R=$CH_3$, n=3, X=O or X=5, Z=Cl, Y=OMe, and A=OC(O)$CH_3$)

A mixture of 6,9-dichloro-2-methoxy-acridine (6.43 g, 23.12 mmol), NN-bis(3-aminopropyl)methylamine (1.67 g, 11.52 mmol) and 4-dimethylaminopyridine (2.82 g, 23.11 mmol) in DMF (100 mL) was stirred at 85°–90° C. for 4 hours under $N_2$. The reaction mixture was filtered and the filtrate was distilled under vacuum to remove DMF. The residue was diluted with chloroform and water to give a solid suspension. The solid was collected and the chloroform solution was washed twice with water, dried, and evaporated. The residue was combined with the solid and chromatographed on silica gel using ethyl acetate as eluent to give the title compound (4.1 g, 56%) as a yellow powder. MP 153.8°–154.5° C., $^1$H NMR (CDCl$_3$, 500 MHz) 7.80–7.95 (m, 6H), 7.00–7.30 (m, 6H), 3.76 (s, 6H), 3.74 (m, 4H), 2.54 (m, 4H), 2.32 (s, 3H), 1.85 (m, 4H). The title compound could also be prepared by the methodology described in Example 5 in comparable yield. The acetic acid salts were prepared by the methodology described in Example 6. MP 128°–129° C., $^1$H NMR (CDCl$_3$, 500 MHz) 7.90 (d, J=9.4 Hz, 2H), 7.57 (d, J=9.4 Hz, 2H), 7.49 (s, 2H), 7.36 (s, 2H), 7.10 (d, J=9.4 Hz, 2H), 6.91 (d, J=9.4 Hz, 2H), 4.04 (t, J=6.5 Hz, 4H), 3.84 (s, 6H), 2.90 (t, J=6.1 Hz, 4H), 2.54 (s, 3H), 2.17 (m, 4H), 2.11 (s, 15H).

EXAMPLE 13

N-alkylated polyamine-linked acridine dimers were prepared according to the method shown in Scheme 2.

Typical example:

Formula I (wherein R=n—$C_3H_7$, n=3, X=5, Z=Cl, Y=OMe, and A=Cl)

To a mixture of a compound of formula I (wherein n=3, and X=0) (0.614 g, 1 mmol)(See Example 5), propionaldehyde (1.47 g, 20.4 mmol), methanol (3 mL), and acetonitrile (3 mL) was added sodium cyanoborohydride (0.7 g) at 0° C. for 0.5 hour and remove the ice-bath. Stirring was continued for 18 hours. The solution was diluted with ethyl acetate and washed with water. The organic layer was evaporated and purified on silica gel using methanol-ethyl acetate-triethylamine (1/10/0.1, v/v) as eluent to give a compound of formula I, wherein n=3, R=n—Pr, and X=0 (0.43 g, 65.5%), which was diluted with small amount of methanol and 5N HCl with stirring and the HCl salt was collected and triturated with acetone to give salt derivatives. MP 192°–194° C., $^1$H NMR (DMSO-$d_6$, 500 MHz) 9.92 (m, 2H, $NH^+$), 9.70 (m, 1H, $NH^+$), 8.35 (m, 2H), 8.00 (m, 2H), 7.82 (s, 2H), 7.74 (d, J=9.5 Hz, 2H), 7.49 (d, J=9.5 Hz, 2H), 7.29 (d, J=9.5 Hz, 2H), 4.08 (m, 2H), 3.83 (s, 6H), 3.20 (m, 4H), 2.94 (m, 2H), 2.35 (m, 4H), 1.60 (m, 2H), 0.78 (t, J=7.0 Hz, 3H).

The following compounds were prepared in a manner similar to the above described procedure except that a different aliphatic aldehyde (i.e. RCHO, R=$C_{1-9}$) or acridine dimer homologue (see, for example, Example 10) was employed for the preparation of N-substituted polyamine-linked acridine. The yields of the acridine dimers is 60–70%. The analytical data are reported as follows:

EXAMPLE 14

Formula I (where in R=ethyl, n=3, Z=Cl, Y=OMe, and X=0)

Foam, $^1$H NMR (CDCl$_3$, 500 MHz) 7.80–8.10 (m, 6H), 7.30 (m, 2H), 7.14 (m, 2H), 7.08 (m, 2H), 3.83 (s, 6H), 3.76 (m, 4H), 2.67 (m, 6H), 1.88 (m, 4H), 1.10 (t, J=7.2 Hz, 3H), MS (20 eV) m/z (rel. intensity) 641.4 ($M^+$($2Cl^{35}$), 100), 467.3(63). The title compound can also be prepared from N-[1-(3-amino-propyl)]-N-[1-(ethyl)]-propane-1,3-diamine (see Example 3) by the methodology described in Example 12.

EXAMPLE 15

Formula I (where in R=ethyl, n=3, X=3.60, Z=Cl, Y=OMe, and A=OC(O)$CH_3$)

Foam, $^1$H NMR (CDCl$_3$, 500 MHz) 7.99 (d, J=10.0 Hz, 2H), 7.61 (d, J=10.0 Hz, 2H), 7.50 (s, 2H), 7.44 (br s, 2H), 7.15 (d, J=10.0 Hz, 2H), 6.97 (d, J=10.0 Hz, 2H), 4.09 (m, 4H), 3.86 (s, 6H), 2.94 (m, 4H), 2.85 (q, J=7.0 Hz, 2H), 2.18 (m, 4H), 2.15 (s, 11.8H), 1.20 (t, J=7.0 Hz, 3H).

EXAMPLE 16

Formula I (wherein R=(cyclopropyl)$CH_2$, n=3, Z=Cl, Y=OMe, and X=0)

Foam, $^1$H NMR (CDCl$_3$, 500 MHz) 7.99 (s, 2H), 7.92 (d, J=9.3 Hz, 2H), 7.90 (s, 2H), 7.33 (m, 2H), 7.19 (s, 2H), 7.12 (m, 2H), 3.80 (s, 6H), 3.79 (t, J=6.5 Hz, 4H), 2.75 (t, J=6.5 Hz, 4H), 2.47 (d, J=6.5 Hz, 2H), 1.89 (t, J=6.5 Hz, 4H), 0.87 (m, 1H), 0.50 (m, 2H), 0.10 (m, 2H), MS (70 eV) m/z (%): 667.5 ($M^+$($2Cl^{35}$), 100), 611.6 (25), 602.3 (33), 499.7 (40), 467.3 (50), 423.2 (50). The title compound could also be prepared from N-[1-(3-amino-propyl)-N-[1-(cyclopropylmethyl)]-propane-1,3-diamine (see Example 4) by the methodology described in Example 12.

EXAMPLE 17

Formula I (wherein R=(cyclopropyl)$CH_2$, n=4, Z=Cl, Y=OMe, and X=0)

Foam, $^1$H NMR (DMSO-$d_6$, 500 MHz) 8.44 (m, 2H), 7.95–7.99 (m, 4H), 7.76 (m, 2H), 7.55 (m, 2H), 7.37 (m, 2H), 4.06 (s, 6H), 3.91 (m, 2H), 3.83 (m, 2H), 2.58 (m, 2H), 2.48 (m, 2H), 2.25 (d, J=6.2 Hz, 2H), 1.90 (m, 2H), 1.73 (m, 2H), 1.45 (m, 2H), 0.70 (m., 1H), 0.38 (m, 2H), 0.02 (m, 2H), MS (70 eV) m/z (%): 681.1 ($M^+$($2Cl^{35}$), 40), 636.9 (20), 423.2 (100).

EXAMPLE 18

Formula I (wherein R=(amyl)$CH_2$, n=3, Z=Cl, Y=OMe, and X=0)

Foam, $^1$H NMR (CDCl$_3$, 500 MHz) 7.80–8.10 (m, 6H), 7.32 (m, 2H), 7.16 (s, 2H), 7.12 (m, 2H), 3.82 (s, 6H), 3.77 (t, J=7.2 Hz, 4H), 2.63 (m, J=7.2 Hz, 4H), 2.52 (m, 2H), 1.87 (t, J=7.2 Hz, 4H), 1.45 (m, 2H), 1.15–1.35 (m, 6H), 0.86 (t, J=7.2 Hz, 4H). The title compound could also be prepared from N-[1-(3-amino-propyl)]-N-[1-(3-amino-propyl)]-N-[1-(hexyl)]-propane-1,3-diamine by the methodology described in Example 12.

EXAMPLE 19

N-(aryl)methyl-, N-(heteroaryl)methyl-, or N-(heterocyclyl)methyl-polyamine-linked acridine dimers were prepared according to Scheme 2.

Typical example:

Formula I (wherein R=$C_6H_5CH_2$, n=3, X=5, Z=Cl, Y=OMe, and A=Cl)

A mixture of formula I (wherein n=3, Z=Cl, Y=OMe, and X=0) (0.614 g, 1 mmol), benzaldehyde (1.0 g, 9.4 mmol), methanol (2 mL), and acetonitrile (4 mL) was added sodium cyanoborohydride (0.4 g) at 0° C. for 0.5 hour and remove the ice-bath. Stirring was continued for 18 hours. The organic layer was evaporated and purified on silica gel using methanol-ethyl acetate-triethylamine (1/10/0.1, v/v) as eluent to give a compound of formula I, wherein n=3, and R=$C_6H_5CH_2$ (0.49 g, 70%), which was diluted with small amount of methanol and 5N HCl with stirring and the HCl salt was collected and triuated with acetone to give the hydrochloride salt of formula I, wherein R=$C_6H_5CH_2$, n=3, X=5, Z=Cl, Y=OMe, and A=Cl. MP 215°–217° C., $^1$H NMR (DMSO-$d_6$, 500 MHz) 9.99 (m, 2H, $NH^+$), 8.47 (m, 2H), 8.10 (m, 2H), 7.93 (s, 2H), 7.65 (d, J=9.5 Hz, 2H), 7.63 (m, 4H), 7.41 (d, J=9.5 Hz, 2H), 7.30 (m, 3H), 4.37 (s, 2H), 4.17 (m, 4H), 3.94 (s, 6H), 3.27 (m, 4H), 2.51 (m, 4H).

In a manner similar to the former procedure except that a different aldehyde (i.e. arylaldehyde, heteroarylaldehyde or heterocyclic carboxaldehyde) or the acridine dimer homologue was employed for the preparation of N-substituted polyamine-linked acridine dimer. The yields of the acridine dimers was 60–70%. The analytic data are reported as follows.

EXAMPLE 20

Formula I (wherein R=$CH_2C_6H_4$(3'-OMe), n=3, Z=Cl, Y=OMe, and X=0)

Foam, $^1$H NMR (CDCl$_3$, 500 MHz) 8.00 (s, 2H), 7.93 (d, J=9.3 Hz, 2H), 7.82 (d, J=9.3 Hz, 2H), 7.35 (d, J=9.3 Hz, 2H), 7.14–7.18 (m, 5H), 6.81 (s, 1H), 6.80 (m, 2H), 3.82 (s, 6H), 3.71 (t, J=6.5 Hz, 4H), 3.65 (s, 2H), 3.57 (s, 2H), 2.58 (t, J=6.5 Hz, 4H), 1.82 (m, 4H), MS (70 eV) m/z (rel. intensity) 734.5 (M$^+$(2Cl$^{35}$)+1, 20), 612.3 (100).

EXAMPLE 21

Formula I (wherein R=CH$_2$C$_6$H$_4$(3'-OMe), n=4, Z=Cl, Y=OMe, and X=0)

Foam, $^1$H NMR (CDCl$_3$, 500 MHz) 8.02 (s, 2H), 7.96 (d, J=9.3 Hz, 2H), 7.85 (d, J=9.3 Hz, 2H), 7.35 (d, J=9.3 Hz, 2H), 7.05–7.30 (m, 6H), 6.70–6.85 (m, 2H), 3.90 (s, 3H), 3.84 (m, 5H), 3.67 (m, 5H), 3.54 (s, 2H), 2.57 (m, 2H), 2.47 (m, 2H), 1.84 (m, 2H), 1.67 (m, 2H), 1.60 (m, 2H), MS (70 eV) m/z (rel. intensity): 747.4 (M$^+$(2Cl$^{35}$), 23), 626.4 (20), 489.3 (100).

EXAMPLE 22

Formula I (wherein R=CH$_2$C$_6$H$_4$(2'-OMe), n=3, Z=Cl, Y=OMe, and X=0)

Foam, $^1$H NMR (CDCl$_3$, 500 MHz) 7.95 (s, 2H), 7.90 (d, J=9.40 Hz, 2H), 7.76 (d, J=9.40 Hz, 2H), 7.25–7.30 (m, 4H), 7.11 (s, 2H), 6.97 (m, 2H), 6.85 (m, 1H), 6.72 (m, 1H), 3.70–3.73 (m, 10H), 3.62 (s, 2H), 3.46 (s, 3H), 2.63 (m, 4H), 1.88 (m, 4H), MS (70 eV) m/z (rel. intensity) 734.4 (M$^+$(2Cl$^{35}$)+1, 8), 612.3 (100).

EXAMPLE 23

Formula I (wherein R=CH$_2$C$_6$H$_4$(4'-OMe), n=4, Z=Cl, Y=OMe, and X=0)

Foam, $^1$H NMR (CDCl$_3$, 500 MHz) 7.80–8.00 (m, 6H), 7.10–7.40 (m, 6H), 7.09 (d, J=8.60 Hz, 2H), 6.76 (d, J=8.60 Hz, 2H), 3.88 (s, 3H), 3.82 (m, 5H), 3.75 (s, 3H), 3.66 (m, 2H), 3.50 (s, 2H), 2.57 (m, 2H), 2.44 (m, 2H), 1.83 (m, 2H), 1.67 (m, 2H), 1.56 (m, 2H), MS (70 eV) m/z (rel. intensity): 747.0 (M$^+$(2Cl$^{35}$), 25), 637.3 (100), 626.6 (40), 488.9 (43).

EXAMPLE 24

Formula I (wherein R=CH$_2$C$_6$H$_3$(2',3'-diOMe), n=3, Z=Cl, Y=OMe, and X=0)

Foam, $^1$H NMR (CDCl$_3$, 500 MHz) 7.96 (d, J=9.3 Hz, 2H), 7.82 (d, J=9.3 Hz, 2H), 7.35 (dd, J=9.3, 2.4 Hz, 2H), 7.14–7.18 (m, 4H), 6.89–6.93 (m, 1H), 6.81–6.83 (m, 2H), 4.13 (s, 3H), 3.83 (s, 6H), 3.78 (s, 3H), 3.74 (m, 4H), 3.68 (s, 2H), 2.62 (m, 4H), 1.87 (m, 4H), MS (70 eV) m/z (rel. intensity): 764.7 (M$^+$(2Cl$^{35}$)+1, 40), 709.3 (40), 692.1 (40), 612.4 (100).

EXAMPLE 25

Formula I (wherein R=CH$_2$C6H$_2$(3',4',5'-triOMe), n=3, Z=Cl, Y=OMe, and X=0)

Foam, $^1$H NMR (CDCl$_3$, 500 MHz) 8.03 (s, 2H), 7.97 (d, J=9.5 Hz, 2H), 7.86 (d, J=9.5 Hz, 2H), 7.38 (m, 2H), 7.16–7.20 (m, 4H), 6.49 (s, 2H), 3.80, 3.82 (each s, 9H), 3.73 (t, J=6.6 Hz, 4H), 3.71 (s, 6H), 3.55 (s, 2H), 2.61 (t, J=6.6 Hz, 4H), 1.84 (m, 4H).

EXAMPLE 26

Formula I (wherein R=CH$_2$C$_6$H$_4$(4'-Cl), n=3, Z=Cl, Y=OMe, and X=0)

Foam, $^1$H NMR (CDCl$_3$, 500 MHz) 7.96 (s, 2H), 7.89 (d, J=9.4 Hz, 2H), 7.77 (d, J=9.4 Hz, 2H), 7.30 (m, 2H), 7.17 (d, J=9.4 Hz, 2H), 7.00–7.16 (m, 6H), 3.77 (s, 6H), 3.62 (t, J=6.6 Hz, 4H), 3.46 (s, 2H), 2.48 (t, J=6.6 Hz, 4H), 1.76 (m, 4H), MS (70 eV) m/z (rel. intensity): 737.1 (M$^+$(3Cl$^{35}$), 5), 612.3 (100).

EXAMPLE 27

ExFormula I (wherein R=CH$_2$C$_6$H$_3$(2',4'-diF), n=3, Z=Cl, Y=OMe, and X=0)

Foam, $^1$H NMR (CDCl$_3$, 500 MHz) 7.98 (s, 2H), 7.92 (d, J=9.40 Hz, 2H), 7.80 (d, J=9.40 Hz, 2H), 7.34 (m, 4H), 7.00–7.15 (m, 5H), 6.71 (m, 2H), 3.79 (s, 6H), 3.64 (m, 4H), 3.58 (s, 2H), 2.52 (m, 4H), 1.79 (m, 4H), MS (70 eV) m/z (rel. intensity): 740.4 (M$^+$(2Cl$^{35}$)+1, 8), 612.3 (100).

EXAMPLE 28

ExFormula I (wherein R=CH$_2$C$_6$H$_3$(2',4'-diF), n=3, X=3.30, Z=Cl, Y=OMe, and A=OC(O)CH$_3$)

Foam, $^1$H NMR (CDCl$_3$, 500 MHz) 8.00 (m, 2H), 7.60 (m, 4H), 7.50 (m, 2H), 7.35 (s, 1H), 7.18 (m, 2H), 6.95 (m, 4H), 3.99 (m, 4H), 3.89 (s, 6H), 3.78 (s, 2H), 2.80 (m, 4H), 2.21 (s, 10H), 2.18 (m, 4H).

EXAMPLE 29

Formula I (wherein R=(CH$_2$)$_2$C$_6$H$_5$, n=3, Z=Cl, Y=OMe, and X=0)

Foam, $^1$H NMR (CDCl$_3$, 500 MHz) 7.94, (s, 2H), 7.87 (d, J=9.5 Hz, 2H), 7.85 (d, J=9.5 Hz, 2H), 7.28 (m, 2H), 7.21 (m, 2H), 7.14 (s, 2H), 7.00–7.10 (m, 5H), 3.07 (s, 6H), 3.70 (t, J=6.4 Hz, 4H), 2.78 (m, 2H), 2.70 (m, 2H), 2.67 (t, J=6.4 Hz, 4H), 1.86 (m, 4H), MS (70 eV) m/z (rel. intensity): 718.4 (M$^+$(2Cl$^{35}$)+1, 40), 626.1 (30), 556.1 (100), 517.4 (55).

EXAMPLE 30

Formula I (wherein R=(CH$_2$)$_3$C$_6$H$_5$, n=3, Z=Cl, Y=OMe, and X=0)

Foam, $^1$H NMR (CDCl$_3$, 500 MHz) 8.00 (s, 2H), 7.94 (d, J=9.50 Hz, 2H), 7.88 (d, J=9.50 Hz, 2H), 7.35 (m, 2H), 7.20–7.30 (m, 2H), 7.05–7.25 (m, 7H), 3.80 (s, 6H), 3.73 (t, J=6.4 Hz, 4H), 2.80 (m, 2H), 2.73 (m, 2H), 2.67 (t, J=6.4 Hz, 4H), 1.87 (m, 2H), 1.85 (m, 4H).

EXAMPLE 31

Formula I (wherein R=CH$_2$(2'-furyl), n=3, Z=Cl, Y=OMe, and X=0)

Foam, $^1$H NMR (CDCl$_3$, 500 MHz) 8.07 (s, 2H), 7.90–8.00 (m, 4H), 7.46 (m, 2H), 7.40 (s, 1H), 7.30–7.20 (m, 4H), 6.40 (s, 1H), 6.26 (s, 1H), 3.95 (s, 6H), 3.87 (t, J=6.5 Hz, 4H), 3.84 (s, 2H), 2.76 (t, J=6.50 Hz, 4H), 1.97 (m, 4H), MS (70 eV) m/z (rel. intensity): 693.4 (M$^+$(2Cl$^{35}$), 6), 614.3 (60), 612.3 (100).

EXAMPLE 32

Formula I (wherein R=CH$_2$(2'-furyl), n=4, Z=Cl, Y=OMe, and X=0)

Foam, $^1$H NMR (CDCl$_3$, 500 MHz) 7.85–8.10 (m, 6H), 7.10–7.50 (m, 7H), 6.39 (s, 1H), 6.26 (s, 1H), 3.98 (m, 2H), 3.96 (s, 6H), 3.80 (m, 2H), 3.79 (s, 2H), 2.75 (m, 2H), 2.63 (m, 2H), 1.94 (m, 2H), 1.82 (m, 2H), 1.75 (m, 2H), MS (70 eV) m/z (rel. intensity): 707.1 (M$^+$(2Cl$^{35}$), 4), 626.4 (2), 436.2 (100).

EXAMPLE 33

Formula I (wherein R=CH$_2$(5'-bromo-2'-furyl), n=3, Z=Cl, Y=OMe, and X=0)

Foam, $^1$H NMR (CDCl$_3$, 500 MHz) 8.02 (s, 2H), 7.95 (d, J=9.5 Hz, 2H), 7.87 (d, J=9.5 Hz, 2H), 7.36 (d, J=9.5 Hz, 2H), 7.22 (d, J=9.5 Hz, 2H), 7.14 (s, 2H), 6.87 (d, J=3.65 Hz, 1H), 6.56 (d, J=3.65 Hz, 1H), 3.86 (s, 6H), 3.71 (s, 2H), 3.68 (t, J=6.6 Hz, 4H), 2.56 (t, J=6.6 Hz, 4H), 1.80 (m, 4H).

EXAMPLE 34

Formula I (wherein R=CH$_2$(5'-ethyl-2'-furyl), n=3, Z=Cl, Y=OMe, and X=0)

Foam, $^1$H NMR (CDCl$_3$, 500 MHz) 8.08 (s, 2H), 8.01 (d, J=9.5 Hz, 2H), 7.97 (d, J=9.5 Hz, 2H), 7.42 (d, J=9.5 Hz, 2H), 7.27 (s, 2H), 7.20 (d, J=9.5 Hz, 2H), 6.12 (d, J=3.0 Hz, 1H), 5.94 (d, J=3.0 Hz, 1H), 3.89 (s, 6H), 3.83 (t, J=6.5 Hz, 4H), 3.77 (s, 2H), 2.74 (t, J=6.5 Hz, 4H), 2.48 (t, J=8.0 Hz, 2H), 1.95 (m, 4H), 1.34 (m, 3H), MS (70 eV) m/z (rel. intensity): 721.0 (M$^+$(2Cl$^{35}$), 10), 625.2 (100), 612.1 (60).

EXAMPLE 35

Formula I (wherein R=CH$_2$(3'-furyl), n=3, Z=Cl, Y=OMe, and X=0)

Foam, $^1$H NMR (CDCl$_3$, 500 MHz) 7.99 (s, 1H), 7.97 (d, J=9.5 Hz, 2H), 7.80–7.90 (m, 5H), 7.30–7.40 (m, 4H), 7.16 (m, 2H), 6.24 (s, 1H), 3.82 (s, 6H), 3.73 (m, 4H), 3.55 (s, 2H), 2.59 (t, J=6.6 Hz, 4H), 1.85 (m, 4H), MS (70 eV) m/z (rel. intensity): 693.2 (100), 614.1 (63), 611.8 (100).

EXAMPLE 36

Formula I (wherein R=CH$_2$(3'-furyl), n=4, Z=Cl, Y=OMe, and X=0)

Foam, $^1$H NMR (CDCl$_3$, 500 MHz) 8.00–7.80 (m, 6H), 7.10–7.40 (m, 8H), 6.23 (s, 1H), 3.86 (s, 6H), 3.82 (m, 2H), 3.65 (m, 2H), 3.50 (s, 2H), 2.57 (m, 2H), 2.45 (m, 2H), 1.81 (m, 2H), 1.67 (m, 2H), 1.57 (m, 2H), MS (70 eV) m/z (rel. intensity): 707.5 (M$^+$(2Cl$^{35}$), 100), 626.1 (20), 636.4 (60), 545.3 (40), 522.0 (27), 493.1 (60), 466.0 (80), 450.1 (100).

EXAMPLE 37

Formula I (wherein R=CH$_2$(3'-furyl), n=3, X=5, Z=Cl, Y=OMe, and A=OC(O)CH$_3$)

Foam, $^1$H NMR (CDCl$_3$, 500 MHz) 7.85 (d, J=9.5 Hz, 2H), 7.40–7.50 (m, 4H), 7.37 (s, 2H), 7.32 (d, J=9.5 Hz, 2H), 7.00 (d, J=9.5 Hz, 2H), 6.83 (d, J=9.5 Hz, 2H), 6.23 (s, 1H), 3.91 (t, J=6.6 Hz, 4H), 3.74.(s, 6H), 2.71 (t, J=6.6 Hz, 4H), 2.01 (m, 4H), 2.00 (m, 15H).

EXAMPLE 38

Formula I (wherein R=CH$_2$(2'-thienyl), n=4, Z=Cl, Y=OMe, and X=0)

Foam, $^1$H NMR (CDCl$_3$, 500 MHz) 8.00 (d, J=3.5 Hz, 1H), 7.99–7.80 (m, 4H), 7.36 (m, 2H), 7.26–7.00 (m, 6H), 6.91 (s, 1H), 3.87 (m, 8H), 3.79 (s, 2H), 3.63 (m, 2H), 2.57 (m, 2H), 2.47 (m, 2H), 1.81 (m, 2H), 1.67 (m, 2H), 1.55 (m, 2H), MS (70 eV) m/z (rel. intensity): 723.2 (M$^+$(2Cl$^{35}$), 57), 626.0 (58), 464.9 (100).

EXAMPLE 39

Formula I (wherein R=CH$_2$(3'-thienyl), n=3, Z=Cl, Y=OMe, and X=0)

Foam, $^1$H NMR (CDCl$_3$, 500 MHz) 8.00 (s, 2H), 7.94 (d, J=9.40 Hz, 2H), 7.84 (d, J=9.40 Hz, 2H), 7.35 (m, 2H), 7.22 (m, 2H), 7.16 (m, 2H), 7.03 (s, 1H), 6.91 (s, 1H), 3.81 (s, 6H), 3.70 (t, J=6.3 Hz, 4H), 3.65 (s, 2H), 2.57 (t, J=6.3 Hz, 2H), 1.81 (m, 4H), MS (70 eV) m/z (rel. intensity): 709.0 (M$^+$(2Cl$^{35}$), 10), 612.3 (10), 450.8 (30), 438.2 (60), 410.1 (100).

EXAMPLE 40

Formula I (wherein R=CH$_2$(3'-thienyl), n=4, Z=Cl, Y=OMe, and X=0)

Foam, $^1$H NMR (CDCl$_3$, 500 MHz) 8.09 (m, 2H), 8.03 (m, 2H), 7.96 (m, 2H), 7.25–7.50 (m, 7H), 7.10 (s, 1H), 7.00 (s, 1H), 3.94 (s, 3H), 3.92 (s, 3H), 3.83 (m, 2H), 3.67 (m, 2H), 3.65 (s, 2H), 2.59 (m, 2H), 2.48 (m,2H), 1.84 (m, 2H), 1.70 (m, 2H), 1.58 (m, 2H), MS (70 eV) m/z (rel. intensity): 723.4 (M$^+$(2Cl$^{35}$), 47), 626.5 (20), 465.2 (100).

EXAMPLE 41

Formula I (wherein R=CH$_2$(3'-methyl-2'-thienyl), n=3, Z=Cl, Y=OMe, and X=0)

Foam, $^1$H NMR (CDCl$_3$, 500 MHz) 8.01 (s, 2H), 7.94 (d, J=9.20 Hz, 2H), 7.82 (d, J=9.20 Hz, 2H), 7.35 (m, 2H), 7.10–7.20 (m, 4H), 7.08 (d, J=5.10 Hz, 1H), 6.76 (d, J=5.10 Hz, 1H), 3.83 (s, 6H), 3.71 (t, J=6.5 Hz, 4H), 3.68 (s, 2H), 2.58 (t, J=6.5 Hz, 4H), 2.10 (s, 3H), 1.81 (m, 4H), MS (70 eV) m/z (rel. intensity): 724.2 (M$^+$(2Cl$^{35}$), 10), 612.4 (100).

EXAMPLE 42

Formula I (wherein R=CH$_2$(3'-methyl-2'-thienyl), n=3, Z=Cl, X=5.0, Y=OMe, and A=OC(O)CH$_3$)

Foam, $^1$H NMR (CDCl$_3$, 500 MHz) 8.17 (d, J=8.5 Hz, 2H), 7.62 (m, 5H), 7.33 (s, 2H), 7.26 (m, 2H), 7.00 (m, 2H), 6.92 (d, J=5.0 Hz, 1H), 4.13 (m, 4H), 3.92 (s, 6H), 3.56 (s, 2H), 2.86 (m, 4H), 2.29 (s, 3H), 2.27 (m, 4H), 2.21 (s, 15H).

EXAMPLE 43

Formula I (wherein R=CH$_2$(5'-bromo-2'-thienyl), n=3, Z=Cl, Y=OMe, and X=0)

Foam, $^1$H NMR (CDCl$_3$, 500 MHz) 8.00 (s, 2H), 7.93 (d, J=9.4 Hz, 2H), 7.85 (d, J=9.4 Hz, 2H), 7.35 (m, 2H), 7.10–7.25 (m, 4H), 6.86 (d, J=3.6 Hz, 1H), 6.55 (d, J=3.6 Hz, 1H), 3.84 (s, 6H), 3.70 (t, J=6.6 Hz, 4H), 2.54 (t, J=6.6 Hz, 4H), 1.78 (m, 4H).

EXAMPLE 44

Formula I (wherein R=CH$_2$(4'-bromo-2'-thienyl), n=3, Z=Cl, Y=OMe, and X=0)

Foam, $^1$H NMR (CDCl$_3$, 500 MHz) 7.95 (s, 2H), 7.88 (d, J=9.5 Hz, 2H), 7.77 (d, J=9.5 Hz, 2H), 7.30 (m, 2H), 7.12 (m, 2H), 7.00–7.15 (m, 3H), 6.72 (s, 1H), 3.79 (s, 6H), 3.70 (s, 2H), 3.64 (t, J=6.5 Hz, 4H), 2.53 (t, J=6.5 Hz, 4H), 1.77 (m, 2H), MS (70 eV) m/z (rel. intensity): 786.5 (M$^+$(2Cl$^{35}$, Br$^{79}$), 10), 612.1 (15), 517.8 (60), 490.0 (100).

EXAMPLE 45

Formula I (wherein R=CH$_2$(2'-pyridyl), n=3, Z=Cl, Y=OMe, and X=0)

Foam, $^1$H NMR (CDCl$_3$, 500 MHz) 8.51 (s, 1H), 8.06 (s, 2H), 7.90–8.00 (m, 4H), 7.57 (m, 1H), 7.40 (m, 2H), 7.00–7.20 (m, 6H), 3.84 (s, 6H), 3.83 (s, 2H), 3.73 (t, J=5.4

Hz, 4H), 2.73 (t, J=5.7 Hz, 4H), 1.92 (m, 4H), MS (70 eV) m/z (rel. intensity): 704.6 (M$^+$(2Cl$^{35}$), 50), 612.1 (100).

EXAMPLE 46

Formula I (wherein R=CH$_2$(3'-pyridyl), n=3, Z=Cl, Y=OMe, and X=0)

Foam, $^1$H NMR (CDCl$_3$, 500 MHz) 8.46 (s, 2H), 7.92 (s, 2H), 7.90 (m, 2H), 7.80 (m, 2H), 7.50–7.00 (m, 8H), 3.79 (s, 6H), 3.63 (t, J=6.70 Hz, 4H), 3.52 (s, 2H), 2.51 (t, J=6.70 Hz, 4H), 1.80 (m, 4H), MS (70 eV) m/z (rel. intensity): 705.3 (M$^+$(2Cl$^{35}$)+1, 17), 621.1 (100), 612.3 (60), 462.1 (55).

EXAMPLE 47

Formula I (wherein R=CH$_2$(2'-pyridyl), n=3, X=5, Z=Cl, Y=OMe, and A=OC(O)CH$_3$)

Foam, $^1$H NMR (CDCl$_3$, 500 MHz) 8.37 (s, 1H), 7.94 (d, J=9.3 Hz, 2H), 7.70 (m, 2H), 7.10–7.60 (m, 7H), 7.09 (d, J=9.3 Hz, 2H), 6.90 (d, J=9.3 Hz, 2H), 3.90 (t, J=6.4 Hz, 4H), 3.76 (s, 2H), 3.75 (s, 6H), 2.85 (m, 4H), 2.14 (s, 15H), 2.09 (m, 4H).

EXAMPLE 48

Formula I (wherein R=CH$_2$(2,2-dimethyl-[1,3]-dioxolan-4-yl), n=3, Z=Cl, Y=OMe, and X=0)

The title compound was prepared by the reductive amination of formula I (wherein R=H, Z=Cl, Y=OMe, n=3, X=0) ) and (R)-2,3-isopropylideneglyceraldehyde. This glyceraldehyde derivative is described in D. Horton, J. B. Hughes and J. K. Thomson, *J. Org. Chem.* Vol. 33, 728 (1968).

Foam, $^1$H NMR (CDCl$_3$, 500 MHz) 7.90–8.10 (m, 6H), 7.40 (m, 2H), 7.10–7.25 (m, 4H), 4.28 (m, 1H), 4.00 (m, 1H), 3.86 (s, 6H), 3.76 (s, 4H), 3.51 (m, 1H), 1.33 (s, 3H), 1.25 (s, 3H), MS (20 eV) m/z (rel. intensity) 727.4 (M$^+$(2Cl$^{35}$), 10), 475.3 (20), 113.2 (100).

EXAMPLE 49

Formula I (wherein R=CH$_2$((5'-(4"-bromophenyl)-2-furyl), n=3, Z=Cl, Y=OMe, and X=0)

Foam, $^1$H NMR (CDCl$_3$, 500 MHz) 7.84–7.78 (m, 6H), 7.28–7.25 (m, 4H), 7.23–7.19 (m, 2H), 7.15 (d, J=2.5 Hz, 2H), 7.02 (d, J=2.5 Hz, 2H), 6.49 (d, J=3.3 Hz, 1H), 6.22 (d, J=3.3 Hz, 1H), 3.82–3.78 (m, 10H), 3.59 (s, 2H), 2.76 (t, J=6.3 Hz, 4H), 1.93 (t, J=6.3 Hz, 4H). MS (electron spray ionization; ESI) m/z (rel. intensity) 848(M+(2Cl$^{35}$, Br$^{79}$)+1, 5), 850(M+(2Cl$^{35}$, Br$^{79}$)+1, 5), 425(100).

EXAMPLE 50

Formula I (wherein R=CH$_2$(t-butyl-(S)-2,2-dimethyl-3-oxazolidinecarboxylate-4-yl), n=3, Z=Cl, Y=OMe, and X=0)

The aldehyde O=CH(t-butyl-(S)-2,2-dimethyl-3-oxazolidinecarboxylate-4-yl) is commercially available.

Foam, $^1$H NMR (CDCl$_3$, 500 MHz) 8.03 (s, 2H), 7.97 (d, J=10 Hz, 3H), 7.91 (d, J=10 Hz, 1H), 7.38 (d, J=7.5 Hz, 2H), 7.25 (d, J=7.5 Hz, 3H), 7.17 (s, 1H), 5.30 (br s, 1H), 3.97 (m, 1H), 3.94 (s, 1H), 3.73–3.60 (m, 7H), 2.66–2.61 (m, 4H), 1.86–1.47 (m, 4H), 1.49 (s, 9H), 1.41 (s, 3H), 1.38 (s, 3H). MS(ESI) m/z (rel. intensity) 827(M+(2Cl$^{35}$)+1, 30), 414 (100). This product can be hydrolyzed to yield a hydroxy amino derivative.

EXAMPLE 51

Formula I (wherein R=CH$_3$, n=3, Z=H, Y=H, X=0)

Foam, $^1$H NMR (DMSO-d$_6$, 500 MHz) 7.00–8.50 (m, 16H), 3.75 (m, 4H), 2.37 (m, 4H), 2.09 (s, 3H), 1.77 (m, 4H).

EXAMPLE 52

Formula I (wherein R=2,3-di(hydroxy)propyl, n=3, Z=Cl, Y=OMe, X=0)

The title compound was prepared from the compound described in Example 48 by hydrolysis (90% CF$_3$CO$_2$H, room temperature), followed by neutralization. Foam, $^1$H NMR (methanol-d$_4$, 200 MHz) 8.00 (d, J=9.2 Hz, 2H), 7.40–7.51 (m, 4H), 7.10–7.20 (m, 4H), 6.98–7.03 (d, J=9.2 Hz, 2H), 3.82 (m, 4H), 3.78 (s, 6H), 3.63 (m, 1H), 3.50 (m, 2H), 2.60–2.80 (m, 4H), 1.90 (m, 4H), MS (70 eV) m/z (rel. intensity): 677.3 (M$^+$(2Cl$^{35}$), 60), 465.2 (80), 421.2 (100).

EXAMPLE 53

Formula I (wherein R=CH$_2$(N-methylpyrrol-2-yl), n=3, Z=Cl, Y=OMe, and X=0)

Foam, $^1$H NMR (CDCl$_3$, 500 MHz) 8.00 (s, 2H), 7.95 (d, J=9.0 Hz, 2H), 7.82 (d, J=9.0 Hz, 2H), 7.36 (d, J=9.2 Hz, 2H), 7.17 (d, J=9.0 Hz, 2H), 7.13 (s, 2H), 6.48 (s, 1H), 6.00 (m, 2H), 3.84 (m, 4H), 3.64 (m, 4H), 3.47 (s, 2H), 3.38 (s, 3H), 2.55 (t, J=7.0 Hz, 4H), 1.72 (t, J=7.0 Hz, 4H). MS(ESI) m/z (rel. intensity) 707(M$^+$(2Cl$^{35}$)+1, 5), 642(5), 614(5), 582(5), 538(10), 494(20), 401(20), 354(68), 322(100).

EXAMPLE 54

Formula I (wherein R=CH$_2$[(s)-2-amino-ethane-1-ol-2-yl], n=3, Z=Cl, Y=OMe, and X=0)

The title compound was prepared from the compound described in Example 50 by hydrolysis (90% CF$_3$CO$_2$H, room temperature), followed by neutralization. Foam, $^1$H NMR (methanol-d$_4$, 500 MHz) 8.03 (d, J=8.3H, 2H), 7.52–7.54 (m, 4H), 7.23–7.28 (m, 4H), 7.04 (d, J=9.3 Hz, 2H), 3.83–4.00 (m, 4H), 3.81 (s, 6H), 3.63 (m, 1H), 3.48 (m, 2H), 2.75 (m, 2H), 2.55–2.70 (m, 4H), 1.91 (m, 4H). MS(ESI) m/z (rel. intensity) 687(M+(2Cl$^{35}$)+1, 10), 466(8), 415(20), 345(100).

EXAMPLE 55

Formula I (wherein

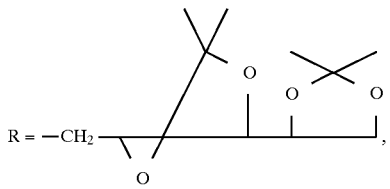

n=3, Z=Cl, Y=OMe, and X=0)

The title compound was prepared by the reductive amination of formula (wherein R=H, Z=Cl, Y=OMe, n=3, X=0)and

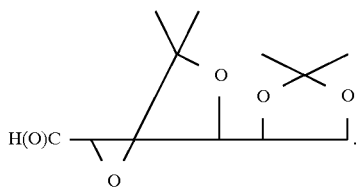

This diketalaldehyde is described in W-L Wu, and Y-L., Wu, J. Org. Chem. Vol 58, 3586(1993). Foam, $^1$H NMR (CDCl$_3$, 500 MHz) 8.09 (m, 2H), 7.88–8.06 (m, 4H), 7.30 (m, 2H), 7.18 (m, 2H), 7.06–7.12 (m, 2H), 4.09–4.14 (m, 2H), 3.92 (m, 3H), 3.79 (s, 6H), 3.73 (m, 4H), 3.43 (m, 1H), 2.92 (m, 1H), 2.72 (m, 4H), 1.86 (m, 4H), 1.34, 1.30, 1.22, 1.16 (each s, 12H). MS(ESI) m/z (rel. intensity) 828(M+(2Cl$^{35}$)+1, 25), 415(100). This product can be hydrolyzed to yield a polyhydroxy derivative.

EXAMPLE 56

The in vitro cytotoxicities of polyamine-linked acridine dimers were examined.

MOLT-4 and COLO 205 cell lines were obtained from American Tissue Culture Company (ATCC), SKBR$_3$ was kindly provided by Anderson Cancer Center, Houston, Tex., U.S.A., and HA22T/VGH was kindly provided by Veterans General Hospital, Taipei, Taiwan, R.O.C. COLO 205 cells were grown as a monolayer and MOLT-4 cells were grown as a suspension in RPMI 1640 with 10% fetal bovine serum (FBS). HA22T/VGH were grown as a monolayer in DMEM/F12 medium supplemented with 10% FBS and 100 μM nonessential amino acid. SKBR$_3$ were grown as a monolayer in DMEM/F12 medium with 10% FBS. Exponentially growing cell cultures were maintained in a humidified atmosphere of 5% CO$_2$-95% air incubator at 37° C.

In principle, the assay depends upon the cellular reduction of MTT by the mitochondrial dehydrogenase of viable cells to a blue formazan product. The viable cell number/well is directly proportional to the production of formazan, which, following solubilization, can be measured spectrophotometrically.

Single cell suspensions were obtained by mechanical disaggregation of the floating cell line (MOLT-4) or by trypsinization of the monolayer cultures (COLO 205, HA22T/VGH, SKBR$_3$) and counted by trypan blue exclusion. The cells were then planted onto 96 well plates in a 180 μL volume using a multichannel pipette and incubated for 24 hours.

Each drug was dissolved in a 10% DMSO and 90% DPBS solution. 20 μL of the drug solution was dispensed within appropriate wells (each treatment group and control, N=3) to make final drug solutions having concentrations between 100 μg/mL and 0.01 μg/mL by 10-fold dilutions. Peripheral wells for each plate (lacking cells) were utilized for drug blank and medium/tetrazolium reagent blank (i.e., for background determinations). The cells were incubated for another 72 hours.

The 20 μL MTT solution (5 mg/mL) was added to each well and incubated for a further 4 hours. Culture plates containing suspension lines or any detached cells were centrifuged at a low speed of 1000 rpm for 5 minutes. The 170 μL culture medium supernatant was removed from each well and replaced with 200 μL/well DMSO using a multichannel pipet. Following thorough formazans solubization (e.g., by vibration on a plate shaker), the absorbance of each well was measured at 545 nm-690 nm using a ELISA automatic plate (Molecular Devices Emax) interfaced with IBM computer Softmax software. Cell growth inhibition was calculated according to the formula (1-(O.D. of drug treatment/O.D. of control)×100%.

The IC$_{50}$ was obtained by 50% growth inhibition at a particular drug concentration by plotting the drug concentration against the growth inhibition percentage. Most acridine bisintercalator derivatives demonstrated good in vitro anticancer activity in human cell lines by these assays. The IC$_{50}$ (μg/mL) values for polyamine linked derivatives were between about 0.04 and 4.94 against HA22T, between about 0.03 and 4.81 against SK-BR-3, between less than 0.01 and about 4.08 against COLO 205, and between less than 0.01 and about 0.5 against MOLT-4.

EXAMPLE 57

DNA intercalating assay

A culture of JM83 bacteria containing a pUC19 plasmid was grown in 500 mL of ampicillin culture medium, and harvested by centrifugation at 4000 rpm for 15 minutes at 4° C. The pellets were lysed by alkali method and the DNA plasmids were collected as the lower band (corresponding to the closed circular DNA) of a centrifuge tube after CsCl-ethidium bromide gradient centrifugation. This collection method is described in, for example, *Molecular Cloning: A Laboratory Manual*, Cold Spring Harbor Laboratory Press, (1989). After removal of ethidium bromide from the DNA plasmids with 1-butanol saturated with water, the CsCl was removed by dialysis with TE (pH 8.0) buffer.

The pUC19 plasmid (1 μg in each reaction) was incubated with various concentrations of solutions containing different polyamine-linked acridine dimers for 30 minutes at 25° C. in 20 μL reaction mixtures (10 mM Tris-HCl, pH 7.4, 0.1 mM EDTA, and 5 mM NaCl). After reaction, the DNA mixture was run on a 1.0% agarose gel, which was stained with ethidium bromide and destained with distilled water. The shifts of the DNA bands were visualized using UV light and analyzed by photography. The DNA band shifting pattern formed a sigmoidal curve. The 50% shift concentration (SC$_{50}$) corresponded to a 50% DNA band shift at the particular concentration, according to the curve of the DNA band-shifting photograph.

5-Fu, a negative control, did not show DNA intercalating activity. The SC$_{50}$ of adriarnycin, a well-known DNA intercalator, was 10–15 μM. Most of the polyamine-linked acridine dimers showed bisintercalating properties, with the exception of compounds of Examples 33 and 43.

EXAMPLE 58

In vivo antitumor activity for human COLO 205 solid tumors

SCID mice (16–18 g, 4–5 weeks old) were obtained from the animal center at the medical center of National Taiwan University, Taipei, R.O.C. and allowed to acclimate to their new environment for one week. The mice were given a sterilized pellet diet and sterilized water ad libitum, and housed under specific pathogene-free conditions in a temperature range between 23°–25° C. and a humidity of about 50±10%. The lighting was automatically operated on a 12 hour light/dark cycle. COLO 205 cells were obtained from ATCC, propagated in culture medium, and subcutaneously inoculated into the dorsal site of the mice.

After solid tumors were grown up to a size of about 1 gram, COLO 205F1 was isolated from the primary culture of the solid tumor and inoculated into the dorsal site of the mice. These tumors were grown to a size of approximately 200 mg (i.e., in a range of 100–300 mg). The mice were sorted according to body weight into groups including five mice. The compounds of Examples 5 and 6 were respectively resuspended in various solvents. The dosage of each compound was intraperitoneally (ip) or intravenously (iv) administered with different schedules. Tumor weights at the beginning of chemotherapy and at weekly intervals thereafter were estimated using two dimensional caliper measurements and calculated with the formula for an ellipsoid. Tumor weight was L X W$^2$×0.5, where L is the major axis and W$_2$ is the width of the tumor. The percentage of tumor growth (%TGI) was calculated according to the formula (1-(mean tumor weight of treated group/mean tumor weight of control group))×100. The tumor weights were corrected for tumor weight at the beginning of treatment. Tumor growth inhibition data were analyzed for statistical significance using the pooled variance t test. The tumor weights were monitored until termination of experiment.

Several studies of salt preparations, different formulations, and various administration routes and schedules were performed for the compounds of example 5 or 6 in order to identify their in vivo antitumor activities for human COLO 205 solid tumors. Tumor growth inhibitor studies of the compound of Example 5 were carried out in 1% carboxymethyl-cellulose against human COLO 205 solid tumors in SCID mice by ip administration with a schedule of Q4D×3 or by iv administration with a schedule of (Q1D×5)×2. Tumor growth inhibition studies of the compound at Example 6 were carried out in distilled H$_2$O against human COLO 205 solid tumor in SCID mice by iv administration with a schedule of (Q2D×3)×2 or in 2.5% cremophor against human COLO 205 solid tumor in SCID mice by iv administration with a schedule of (Q2D×3)×2.

The compound of Example 5 (a free base) dissolved in 1% carboxymethyl-cellulose did not show in vivo antitumor activity for human COLO 205 solid tumors administered by the ip route with Q4D×3 schedule or the iv route with (Q1D×5)×2 schedule.

The compound of Example 6 is an acetate salt of the compound of Example 6. The compound of Example 6 dissolved in distilled H$_2$O and demonstrated in vivo antitumor activity for human COLO 205 solid tumors by iv administration with a schedule of (Q2D×3)×2. When the compound of Example 6 was dissolved in 2.5% cremophor, it had the dose-response relationship of in vivo antitumor activity for human COLO 205 solid tumors.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and, without departing from the spirit and scope thereof, can make various changes and modifications of the invention to adapt it to various usages and conditions. Thus, other embodiments are also within the claims.

What is claimed is:
1. A compound of the following formula

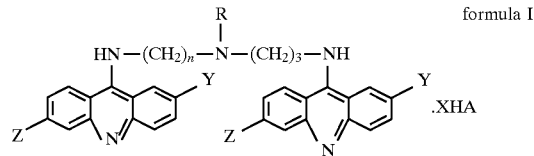

wherein
n is 3, 4, 5, 6; X is between 0 and 5, inclusive; Z is H, F, Cl, Br, or I; Y is H or OR', wherein R' is H or C$_{1-4}$ alkyl; A is OC(O)CH$_3$, OC(O)CF$_3$, OSO$_2$CH$_3$, or halogen; and R is C$_{1-10}$ hydroxvalkyl, C$_{1-10}$ polyhydroxyalkyl, C$_{1-10}$ aminoalkyl, C$_{1-10}$ aminohydroxyalkyl, C$_{1-10}$ haloalkyl, or (CH$_2$)$_y$R", wherein y is 1, 2, or 3, and R" is aryl, substituted aryl, heteroaryl, substituted heteroaryl, heterocyclyl, or substituted heterocyclyl.

2. A compound of the following formula

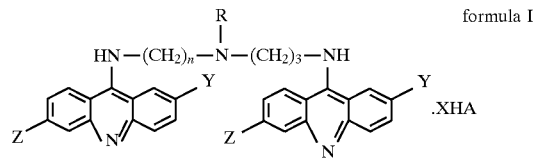

wherein n is 3, 4, 5, or 6; X is between 0 and 5, inclusive; Z is H, F, Cl, Br, or I; Y is H or OR', wherein R' is H or C$_{1-4}$ alkyl; A is OC(O)CH$_3$, OC(O)CF$_3$, OSO$_2$CH$_3$, or halogen; and R is CH$_2$C$_6$H$_5$, (CH$_2$)$_2$C$_6$H$_5$, (CH$_2$)$_3$C$_6$H$_5$, CH$_2$C$_6$H$_4$ (2'-OMe), CH$_2$C$_6$H$_4$(3'-OMe), CH$_2$C$_6$H$_3$(2',3'-diOMe), CH$_2$C$_6$H$_2$(3',4',5'-triOMe), CH$_2$C$_6$H$_4$(4'-Cl), or [CH$_2$C$_2$H$_3$ (2',4'-diF)] CH$_2$C$_6$H$_3$(2'4'-diF).

3. A compound of the following formula

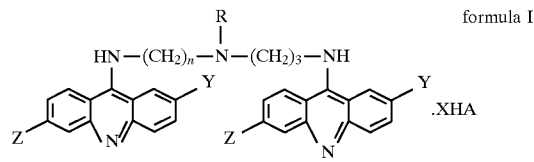

wherein n is 3, 4, 5, or 6; X is between 0 and 5, inclusive; Z is H, F, Cl, Br, or I; Y is H or OR', wherein R' is H or C$_{1-4}$ alkyl; A is OC(O)CH$_3$, OC(O)CF$_3$, OSO$_2$CH$_3$, or halogen; and R is (CH$_2$)$_y$R", y is 1, and R" is heteroaryl, substituted heteroaryl, heterocyclyl, or substituted heterocyclyl.

4. The compound of claim 3, wherein R" is furyl, pyridyl, thienyl, pyrrolyl, a C$_{1-4}$ alkyl-substituted furyl, a C$_{1-4}$ alkyl-substituted pyrrolyl, a C$_{1-4}$ alkyl-substituted pyridyl, a C$_{1-4}$ alkyl-substituted thienyl, a C$_{1-4}$ alkyl-substituted pyridyl, an aryl-substituted furyl, a substituted aryl-substituted frryl, a halogen-substituted furyl, a halogen-substituted pyridyl, a halogen-substituted thienyl.

5. The compound of claim 3, wherein R" is dioxolanyl, oxazolidinyl, substituted dioxolanyl, or substituted oxazolidinyl.

6. The compound of claim 1, wherein X is between 1 and 5, inclusive.

7. The compound of claim 1, wherein n is 3 or 4.

8. The compound of claim 1, wherein A is Cl or OC(O) CH$_3$.

9. A method of preparing a compound of the following formula

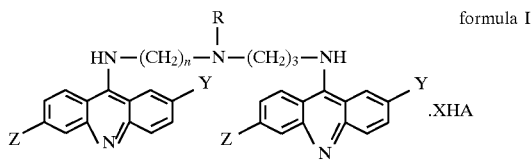

formula I wherein n is 3, 4, 5, or 6; X is 0; z is H, F, Cl, Br, or I; Y is H or OR', wherein R' is H or $C_{1-4}$ alkyl; A is $OC(C)CH_3$, $OC(O)CF_3$, $OSO_2CH_3$, or halogen; and R is $C_{1-10}$ hydroxyalkyl, $C_{1-10}$ polyhydroxyalkyl, $C_{1-10}$ aminoalkyl, $C_{1-10}$ aminohydroxyalkyl, $C_{1-10}$ haloalkyl, or $(CH_2)_yR''$, wherein y is 1, 2, or 3, and R'' is aryl, substituted aryl, heteroaryl, substituted heteroaryl, heterocyclyl, or substituted heterocyclyl, said method comprising contacting a compound of a formula, $H_2N—(CH_2)_n—NR—(CH_2)_3—NH_2$, with a 9-chloro-acridine to form a product compound of formula I wherein X is 0.

10. The method of claim 9, wherein the 9-chloro acridine is 6,9-dichloro-2-methoxy acridine.

11. The method of claim 9, further comprising forming a salt between the product compound of formula I and an acid HA to give a product salt of formula I wherein X is between 1 and 5, inclusive.

12. The method of claim 9, wherein R is $(CH_2)_yR''$, y is 1, and R'' is heteroaryl, substituted heteroaryl, heterocyclyl or substituted heterocyclycl.

13. The method of claim 9, wherein the $H_2N—(CH_2)_n—NR—(CH_2)_3—NH_2$ is prepared by the reductive amination of $NC—(CH_2)_n—NR—(CH_2)_3—CN$ with an aldehyde to form a intermediate followed by reduction of the nitrites of the intermediate.

14. A method of preparing a compound of the following formula

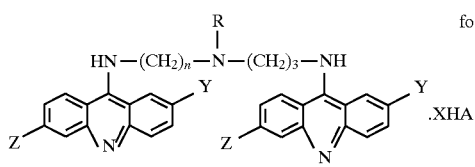

formula I wherein n is 3, 4, 5, or 6; X is between 0 and 5, inclusive; Z is H, F, Cl, Br, or I; Y is H or OR', wherein R' is H or $C_{1-4}$ alkyl; A is $OC(O)CH_3$, $OC(O)CF_3$, $OSO_2CH_3$, or halogen; and R is $C_{1-10}$ hydroxyalkyl, $C_{1-10}$ polyhydroxyalkyl, $C_{1-10}$ aminoalkyl, $C_{1-10}$ aminohydroxyalkyl, $C_{1-10}$ haloalkyl, or $(CH_2)_yR''$, wherein y is 1, 2, or 3, and R'' is aryl, substituted aryl, heteroaryl, substituted heteroaryl, heterocyclyl, or substituted heterocyclyl, said method comprising:

reductive aminating a compound of the following formula,

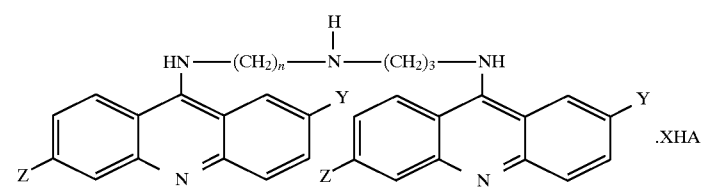

wherein n is 3, 4, 5, or 6, and X is 0 with an aldehyde to form a product compound of formula I, wherein n is 3, 4, 5, or 6; X is 0; Z is H, F, Cl, Br, or I; Y is H or OR', wherein R' is H or $C_{1-4}$ alkyl; A is $OC(O)CH_3$, $OC(O)CF_3$, $OSO_2CH_3$, or halogen; and R is $C_{1-10}$ hydroxyalkyl, $C_{1-10}$ polyhydroxyalkyl, $C_{1-10}$ aminoalkyl, $C_{1-10}$ aminohydroxyalkyl, $C_{1-10}$ haloalkyl, or $(CH_2)_yR''$, wherein y is 1, 2, or 3, and R'' is aryl, substituted aryl, heteroaryl, substituted heteroaryl, heterocyclyl, or substituted heterocyclyl.

15. The method of claim 14, further comprising forming a salt between the product compound of formula I and an acid HA to give a product salt of formula I wherein X is between 1 and 5, inclusive.

16. The compound of claim 1, wherein R is $C_{1-10}$ hydroxyalkyl, $C_{1-10}$ polyhydroxyalkyl, or $(CH_2)_y R''$; wherein y is 1 and R'' is heterocyclyl, or substituted heterocyclyl.

* * * * *